(12) United States Patent
Bales, Jr. et al.

(10) Patent No.: US 10,463,509 B2
(45) Date of Patent: *Nov. 5, 2019

(54) HELICAL STENT HAVING IMPROVED FLEXIBILITY AND EXPANDABILITY

(71) Applicant: C. R. Bard, Inc., Murray Hill, NJ (US)

(72) Inventors: Thomas O. Bales, Jr., Miami, FL (US); Peter K. Kratsch, Leander, TX (US); Kenneth E. Perry, Bainbridge Island, WA (US)

(73) Assignee: C. R. Bard, Inc., Murray Hill, NJ (US)

( * ) Notice: Subject to any disclaimer, the term of this patent is extended or adjusted under 35 U.S.C. 154(b) by 334 days.

This patent is subject to a terminal disclaimer.

(21) Appl. No.: 15/378,483

(22) Filed: Dec. 14, 2016

(65) Prior Publication Data

US 2017/0086994 A1   Mar. 30, 2017

Related U.S. Application Data

(63) Continuation of application No. 13/970,474, filed on Aug. 19, 2013, now Pat. No. 9,554,927, which is a
(Continued)

(51) Int. Cl.
*A61F 2/88* (2006.01)
*A61F 2/915* (2013.01)

(52) U.S. Cl.
CPC .............. *A61F 2/88* (2013.01); *A61F 2/915* (2013.01); *A61F 2002/91508* (2013.01);
(Continued)

(58) Field of Classification Search
CPC .. A61F 2/88; A61F 2/915; A61F 2002/91508; A61F 2002/91516;
(Continued)

(56) References Cited

U.S. PATENT DOCUMENTS 4,886,062 A    12/1989  Wiktor
5,091,205 A    2/1992   Fan
(Continued)

FOREIGN PATENT DOCUMENTS

CA    2155527 A1    8/1994
DE    02544371 A1   4/1976
(Continued)

OTHER PUBLICATIONS

CA 2,640,234 Office Action dated Feb. 14, 2014.
(Continued)

*Primary Examiner* — Christopher D. Prone
*Assistant Examiner* — Tiffany P Shipmon
(74) *Attorney, Agent, or Firm* — Rutan & Tucker, LLP

(57) ABSTRACT

A stent includes a central portion of helically wound undulations formed of struts, cylindrical end portions, and transition zones between the helical portion and the cylindrical portions. According to a first aspect of the invention, the torsional flexibility of the stent is maximized by having bridges connecting adjacent windings be interrupted by the maximum possible number of undulations. In one embodiment, each winding includes nineteen undulations around the circumference; bridges are provided every five undulations. According to a second aspect of the invention, uniform opening of the transition zone is achieved by altering the width, and thereby the flexibility, of a series of struts in accordance with their lengths. Specifically, the long transition zone struts are made wider.

15 Claims, 3 Drawing Sheets

Related U.S. Application Data continuation of application No. 11/074,806, filed on Mar. 8, 2005, now Pat. No. 8,512,391, which is a continuation of application No. 10/231,666, filed on Aug. 30, 2002, now Pat. No. 6,878,162.

(52) U.S. Cl.
CPC ............. *A61F 2002/91516* (2013.01); *A61F 2002/91525* (2013.01); *A61F 2002/91533* (2013.01); *A61F 2002/91558* (2013.01); *A61F 2002/91583* (2013.01); *A61F 2250/0036* (2013.01); *A61F 2250/0037* (2013.01); *A61F 2250/0098* (2013.01)

(58) Field of Classification Search
CPC .. A61F 2002/91525; A61F 2002/91533; A61F 2002/91558; A61F 2002/91583; A61F 2250/0036; A61F 2250/0037; A61F 2250/0098
See application file for complete search history.

(56) References Cited

U.S. PATENT DOCUMENTS

| | | |
|---|---|---|
| 5,292,331 A | 3/1994 | Boneau |
| 5,314,472 A | 5/1994 | Fontaine |
| 5,356,423 A | 10/1994 | Tihon et al. |
| 5,370,683 A | 12/1994 | Fontaine |
| 5,421,955 A | 6/1995 | Lau et al. |
| 5,514,154 A | 5/1996 | Lau et al. |
| 5,540,712 A | 7/1996 | Kleshinski et al. |
| 5,562,697 A | 10/1996 | Christiansen |
| 5,569,295 A | 10/1996 | Lam |
| 5,591,197 A | 1/1997 | Orth et al. |
| 5,630,829 A | 5/1997 | Lauterjung |
| 5,649,952 A | 7/1997 | Lam |
| 5,653,727 A | 8/1997 | Wiktor |
| 5,665,115 A | 9/1997 | Cragg |
| 5,716,393 A | 2/1998 | Lindenberg et al. |
| 5,716,396 A | 2/1998 | Williams, Jr. |
| 5,725,572 A | 3/1998 | Lam et al. |
| 5,741,327 A | 4/1998 | Frantzen |
| 5,776,161 A | 7/1998 | Globerman et al. |
| 5,780,807 A | 7/1998 | Saunders |
| 5,800,456 A | 9/1998 | Maeda et al. |
| 5,800,520 A | 9/1998 | Fogarty et al. |
| 5,810,870 A | 9/1998 | Myers et al. |
| 5,810,872 A | 9/1998 | Kanesaka et al. |
| 5,824,043 A | 10/1998 | Cottone, Jr. |
| 5,824,059 A | 10/1998 | Wijay |
| 5,843,175 A | 12/1998 | Frantzen |
| 5,861,027 A | 1/1999 | Trapp |
| 5,868,781 A | 2/1999 | Killion |
| 5,879,381 A | 3/1999 | Moriuchi et al. |
| 5,891,191 A | 4/1999 | Stinson |
| 5,895,406 A | 4/1999 | Gray et al. |
| 5,902,317 A | 5/1999 | Kleshinski et al. |
| 5,906,639 A | 5/1999 | Rudnick et al. |
| 5,911,754 A | 6/1999 | Kanesaka et al. |
| 5,913,897 A | 6/1999 | Corso, Jr. et al. |
| 5,922,021 A | 7/1999 | Jang |
| 5,925,061 A | 7/1999 | Ogi et al. |
| 5,935,162 A | 8/1999 | Dang |
| 5,968,088 A | 10/1999 | Hansen et al. |
| 5,985,061 A | 11/1999 | Doi et al. |
| 6,013,854 A | 1/2000 | Moriuchi |
| 6,019,789 A | 2/2000 | Dinh et al. |
| 6,022,374 A | 2/2000 | Imran |
| 6,042,597 A | 3/2000 | Kveen et al. |
| 6,042,605 A | 3/2000 | Martin et al. |
| 6,053,940 A | 4/2000 | Wijay |
| 6,059,808 A | 5/2000 | Boussignac et al. |
| 6,059,822 A | 5/2000 | Kanesaka et al. |
| 6,063,113 A | 5/2000 | Kavteladze et al. |
| 6,066,167 A | 5/2000 | Lau et al. |
| 6,117,165 A | 9/2000 | Becker |
| 6,129,755 A | 10/2000 | Mathis et al. |
| 6,190,406 B1 | 2/2001 | Duerig et al. |
| 6,203,568 B1 | 3/2001 | Lombardi et al. |
| 6,238,409 B1 | 5/2001 | Hojeibane |
| 6,238,430 B1 | 5/2001 | Klumb et al. |
| 6,245,100 B1 | 6/2001 | Davila et al. |
| 6,248,122 B1 | 6/2001 | Klumb et al. |
| 6,251,135 B1 | 6/2001 | Stinson et al. |
| 6,273,911 B1 | 8/2001 | Cox et al. |
| 6,293,966 B1 | 9/2001 | Frantzen |
| 6,315,794 B1 | 11/2001 | Richter |
| 6,325,820 B1 | 12/2001 | Khosravi et al. |
| 6,342,067 B1 | 1/2002 | Mathis et al. |
| 6,348,065 B1 | 2/2002 | Brown et al. |
| 6,352,552 B1 | 3/2002 | Levinson et al. |
| 6,361,557 B1 | 3/2002 | Gittings et al. |
| 6,423,091 B1 | 7/2002 | Hojeibane |
| 6,475,236 B1 | 11/2002 | Roubin et al. |
| 6,485,509 B2 | 11/2002 | Killion et al. |
| 6,485,511 B2 | 11/2002 | Lau et al. |
| 6,488,700 B2 | 12/2002 | Klumb et al. |
| 6,488,701 B1 | 12/2002 | Nolting et al. |
| 6,488,703 B1 | 12/2002 | Kveen et al. |
| 6,503,271 B2 | 1/2003 | Duerig et al. |
| 6,517,570 B1 | 2/2003 | Lau et al. |
| 6,520,987 B1 | 2/2003 | Plante |
| 6,527,938 B2 | 3/2003 | Bales et al. |
| 6,533,807 B2 | 3/2003 | Wolinsky et al. |
| 6,537,310 B1 | 3/2003 | Palmaz et al. |
| 6,551,351 B2 | 4/2003 | Smith et al. |
| 6,572,647 B1 | 6/2003 | Supper et al. |
| 6,585,755 B2 | 7/2003 | Jackson et al. |
| 6,613,081 B2 | 9/2003 | Kim et al. |
| 6,645,237 B2 | 11/2003 | Klumb et al. |
| 6,656,219 B1 | 12/2003 | Wiktor |
| 6,660,019 B1 | 12/2003 | Richter et al. |
| 6,660,032 B2 | 12/2003 | Klumb et al. |
| 6,692,522 B1 | 2/2004 | Richter |
| 6,702,807 B2 | 3/2004 | Peyman |
| 6,719,782 B1 | 4/2004 | Chuter |
| 6,730,116 B1 | 5/2004 | Wolinsky et al. |
| 6,733,524 B2 | 5/2004 | Tseng et al. |
| 6,740,114 B2 | 5/2004 | Burgermeister |
| 6,755,856 B2 | 6/2004 | Fierens et al. |
| 6,776,793 B2 | 8/2004 | Brown et al. |
| 6,776,794 B1 | 8/2004 | Hong et al. |
| 6,814,746 B2 | 11/2004 | Thompson et al. |
| 6,852,124 B2 | 2/2005 | Cox et al. |
| 6,862,794 B2 | 3/2005 | Hopkins |
| 6,863,685 B2 | 3/2005 | Davila et al. |
| 6,866,669 B2 | 3/2005 | Buzzard et al. |
| 6,878,162 B2 | 4/2005 | Bales et al. |
| 6,918,928 B2 | 7/2005 | Wolinsky et al. |
| 6,923,828 B1 | 8/2005 | Wiktor |
| 6,929,660 B1 | 8/2005 | Ainsworth et al. |
| 6,935,404 B2 | 8/2005 | Duerig et al. |
| 6,939,352 B2 | 9/2005 | Buzzard et al. |
| 6,949,120 B2 | 9/2005 | Kveen et al. |
| 6,969,402 B2 | 11/2005 | Bales et al. |
| 6,976,994 B2 | 12/2005 | Ballou et al. |
| 7,004,968 B2 | 2/2006 | Lootz et al. |
| 7,025,777 B2 | 4/2006 | Moore |
| 7,033,385 B2 | 4/2006 | Eder et al. |
| 7,034,821 B2 | 4/2006 | Baumberg |
| 7,037,330 B1 | 5/2006 | Rivelli, Jr. et al. |
| 7,037,331 B2 | 5/2006 | Mitelberg et al. |
| 7,128,752 B2 | 10/2006 | Bales |
| 7,131,993 B2 | 11/2006 | Gregorich |
| 7,169,175 B2 | 1/2007 | Cottone, Jr. et al. |
| 7,172,623 B2 | 2/2007 | Hansen et al. |
| 7,195,648 B2 | 3/2007 | Jones et al. |
| 7,214,229 B2 | 5/2007 | Mitchell et al. |
| 7,243,408 B2 | 7/2007 | Vietmeier |
| 7,273,494 B2 | 9/2007 | Rolando et al. |
| 7,326,245 B2 | 2/2008 | Rosenthal et al. |
| 7,331,986 B2 | 2/2008 | Brown et al. |
| 7,758,624 B2 | 7/2010 | Dorn et al. |

(56) References Cited

U.S. PATENT DOCUMENTS

| | | |
|---|---|---|
| 7,763,066 B2 | 7/2010 | Parker |
| 7,763,067 B2 | 7/2010 | Bales et al. |
| 7,771,411 B2 | 8/2010 | Smith et al. |
| 7,780,721 B2 | 8/2010 | Bales et al. |
| 7,972,355 B2 | 7/2011 | Bales |
| 7,993,384 B2 | 8/2011 | Wu et al. |
| 8,002,818 B2 | 8/2011 | Bregulla |
| 8,038,707 B2 | 10/2011 | Bales et al. |
| 8,070,794 B2 | 12/2011 | Issenmann |
| 8,328,865 B2 | 12/2012 | Bales, Jr. et al. |
| 8,333,799 B2 | 12/2012 | Bales, Jr. et al. |
| 8,512,391 B2 | 8/2013 | Bales, Jr. et al. |
| 8,628,563 B2 | 1/2014 | Fliedner |
| 8,672,994 B2 | 3/2014 | Kaplan et al. |
| 8,876,888 B2 | 11/2014 | Lee et al. |
| 9,049,360 B2 | 6/2015 | Jo et al. |
| 9,456,911 B2 | 10/2016 | Bales, Jr. et al. |
| 9,486,339 B2 | 11/2016 | Bales, Jr. et al. |
| 2002/0035394 A1 | 3/2002 | Fierens et al. |
| 2002/0143386 A1 | 10/2002 | Davila et al. |
| 2002/0183826 A1 | 12/2002 | Dorn et al. |
| 2002/0183831 A1 | 12/2002 | Rolando et al. |
| 2002/0198601 A1 | 12/2002 | Bales et al. |
| 2003/0040754 A1 | 2/2003 | Mitchell et al. |
| 2003/0050690 A1 | 3/2003 | Kveen et al. |
| 2003/0055485 A1 | 3/2003 | Lee et al. |
| 2003/0074054 A1 | 4/2003 | Duerig et al. |
| 2003/0093066 A1 | 5/2003 | Peyman |
| 2003/0108659 A1 | 6/2003 | Bales et al. |
| 2003/0176914 A1 | 9/2003 | Rabkin et al. |
| 2003/0216807 A1 | 11/2003 | Jones et al. |
| 2004/0015229 A1 | 1/2004 | Fulkerson et al. |
| 2004/0034402 A1 | 2/2004 | Bales et al. |
| 2004/0044399 A1 | 3/2004 | Ventura |
| 2004/0044401 A1 | 3/2004 | Bales et al. |
| 2004/0054398 A1 | 3/2004 | Cully et al. |
| 2004/0073291 A1 | 4/2004 | Brown et al. |
| 2004/0093066 A1 | 5/2004 | Durcan |
| 2004/0122466 A1 | 6/2004 | Bales |
| 2004/0153142 A1 | 8/2004 | Klumb et al. |
| 2004/0172127 A1 | 9/2004 | Kantor |
| 2004/0267353 A1 | 12/2004 | Gregorich |
| 2005/0060025 A1 | 3/2005 | Mackiewicz et al. |
| 2005/0090890 A1 | 4/2005 | Wu et al. |
| 2005/0107738 A1 | 5/2005 | Slater et al. |
| 2005/0107865 A1 | 5/2005 | Clifford et al. |
| 2005/0113798 A1 | 5/2005 | Slater et al. |
| 2005/0159807 A1 | 7/2005 | Bales et al. |
| 2006/0004437 A1 | 1/2006 | Jayaraman |
| 2006/0060266 A1 | 3/2006 | Bales et al. |
| 2006/0064154 A1 | 3/2006 | Bales et al. |
| 2006/0064155 A1 | 3/2006 | Bales et al. |
| 2006/0064158 A1 | 3/2006 | Bales et al. |
| 2006/0074480 A1 | 4/2006 | Bales et al. |
| 2006/0195175 A1 | 8/2006 | Bregulla |
| 2006/0211979 A1 | 9/2006 | Smith et al. |
| 2007/0049965 A1 | 3/2007 | Bales |
| 2007/0255094 A1 | 11/2007 | Oepen et al. |
| 2008/0039919 A1 | 2/2008 | Kaplan et al. |
| 2009/0036964 A1 | 2/2009 | Heringes et al. |
| 2009/0204200 A1 | 8/2009 | Bales, Jr. et al. |
| 2009/0204203 A1 | 8/2009 | Allen et al. |
| 2009/0264986 A1 | 10/2009 | Bales et al. |
| 2010/0004725 A1 | 1/2010 | Zipse et al. |
| 2010/0298921 A1 | 11/2010 | Schlun et al. |
| 2012/0303112 A1 | 11/2012 | Armstrong et al. |
| 2013/0090719 A1 | 4/2013 | Bales, Jr. et al. |
| 2013/0090721 A1 | 4/2013 | Bales, Jr. et al. |
| 2013/0238084 A1 | 9/2013 | Bales, Jr. et al. |
| 2013/0325141 A1 | 12/2013 | Gill et al. |
| 2013/0338759 A1 | 12/2013 | Bales, Jr. et al. |
| 2016/0058590 A1 | 3/2016 | Mukai |
| 2017/0014249 A1 | 1/2017 | Bales, Jr. et al. |
| 2018/0140444 A1 | 5/2018 | Neuss et al. |

FOREIGN PATENT DOCUMENTS

| | | | |
|---|---|---|---|
| DE | 29516712 U1 | 12/1995 | |
| DE | 19539449 A1 | 4/1997 | |
| DE | 29522101 | 12/1999 | |
| DE | 19901530 A1 | 7/2000 | |
| DE | 20019429 U1 | 3/2002 | |
| DE | 69521346 T2 | 4/2002 | |
| EP | 0688545 A1 | 12/1995 | |
| EP | 0712614 A1 | 5/1996 | |
| EP | 0732088 A2 | 9/1996 | |
| EP | 0790041 A2 | 8/1997 | |
| EP | 0792627 A2 | 9/1997 | |
| EP | 0945107 A | 9/1999 | |
| EP | 1132058 A1 | 9/2001 | |
| EP | 1155664 A2 | 11/2001 | |
| FR | 2760351 A1 | 9/1998 | |
| WO | 1996018359 A1 | 6/1996 | |
| WO | 1996028116 A1 | 9/1996 | |
| WO | 98/30173 A1 | 7/1998 | |
| WO | 1998038945 A1 | 9/1998 | |
| WO | WO 00/16718 | * 9/1998 | ............... A61F 2/06 |
| WO | 2000024340 A1 | 5/2000 | |
| WO | 2000049973 A2 | 8/2000 | |
| WO | 2000050116 A1 | 8/2000 | |
| WO | 2001023102 A1 | 5/2001 | |
| WO | 2001089421 | 11/2001 | |
| WO | 2004109818 A1 | 12/2004 | |
| WO | 2006005026 A2 | 1/2006 | |
| WO | 2006026777 A2 | 3/2006 | |
| WO | 2006026778 A2 | 3/2006 | |
| WO | 2006026779 A2 | 3/2006 | |
| WO | 2006026781 A2 | 3/2006 | |
| WO | 2006026782 A2 | 3/2006 | |
| WO | 2007003591 A1 | 1/2007 | |
| WO | 2007095466 A2 | 8/2007 | |
| WO | 2008100780 A2 | 8/2008 | |
| WO | 2008100783 A2 | 8/2008 | |

OTHER PUBLICATIONS

CA 2948428 filed Feb. 9, 2007 Office Action dated May 31, 2018.
Designation: ASTM F67-06 Standard Specification for Unalloyed Titanium, for Surgical Implant Applications (UNS R50250, UNS R50400, UNS R50550, UNS R50700) Active Standard ASTM F67 Developed by Subcommittee: F04.12, Book of Standards vol. 13.01.
Designation: ASTM B348-05 Standard Specification for Titanium and Titanium Alloy Bars and Billets Active Standard ASTM B348 Developed by Subcommittee: B10.01, Book of Standards vol. 02.04.
EP 03790935.5 Notice of Intent to Grant dated Mar. 27, 2014.
EP 05796577.4 European Seach Report dated Feb. 12, 2011.
EP 05796752.3 European Search Report dated Mar. 26, 2013.
EP 07717595.8 European Search Report dated Nov. 4, 2013.
EP Application No. 05810201 filed Jan. 19, 2005 EP Search Report dated Aug. 7, 2008.
EP Application No. 10177855.3 filed Aug. 26, 2003 Examination Report dated Apr. 12, 2012.
Haas, Schuessler, Welding and Joining of TiNi Shape Memory Alloys: Engineering Aspects and Medical Applications. Proceedings First European Conference on Shape Memory and Superelastic Technolgoies SMST-99, Belguim (1999).
Kastrati, A. Clinical Impact of Stent Design 2: Results From Randomized Trials TCT2003.
PCT/DE1999/002980 filed Sep. 20, 1999 Search Report dated Feb. 3, 2000.
PCT/EP20031009570 filed Aug. 26, 2003 Search Report dated Mar. 11, 2004.
PCT/US2005/031556 filed Sep. 1, 2005 International Preliminary Report on Patentability dated Feb. 24, 2009.
PCT/US2005/031556 filed Sep. 1, 2005 Search Report on Patentability dated Jan. 17, 2008.
PCT/US2005/031556 filed Sep. 1, 2005 Written Opinion dated Jan. 6, 2008.

(56) References Cited

OTHER PUBLICATIONS

PCT/US2005/031557 filed Sep. 1, 2005 International Preliminary Report on Patentability dated Oct. 16, 2007.
PCT/US2005/031557 filed Sep. 1, 2005 Search Report dated Sep. 25, 2007.
PCT/US2005/031557 filed Sep. 1, 2005 Written Opinion dated Sep. 13, 2997.
PCT/US2005/031571 filed Sep. 1, 2005 International Preliminary Report on Patentability dated Mar. 6, 2007.
PCT/US2005/031571 filed Sep. 1, 2005 Search Report dated Aug. 30, 2006.
PCT/US2005/031571 filed Sep. 1, 2005 Written Opinion dated Jul. 14, 2006.
PCT/US2005/031618 filed Sep. 1, 2005 International Preliminary Report on Patentability dated Nov. 6, 2007.
PCT/US2005/031618 filed Sep. 1, 2005 Search Report dated Sep. 20, 2007.
PCT/US2005/031618 filed Sep. 1, 2005 Written Opinion dated Jul. 9, 2007.
PCT/US2005/031619 filed Sep. 1, 2005 International Preliminary Report on Patentability dated Sep. 11, 2007.
PCT/US2005/031619 filed Sep. 1, 2005 Search Report dated Jul. 27, 2007.
PCT/US2005/031619 filed Sep. 1, 2005 Written Opinion dated Jul. 13, 2007.
PCT/US2007/061917 filed Dec. 9, 2007 International Preliminary Report on Patentability dated Aug. 19, 2008.
PCT/US2007/061917 filed Dec. 9, 2007 Search Report dated Mar. 17, 2008.
PCT/US2007/061917 filed Dec. 9, 2007 Written Opinion dated Mar. 17, 2008.
PCT/US2008/053319 filed Feb. 7, 2008 International Preliminary Report on Patentability dated Aug. 19, 2009.
PCT/US2008/053319 filed Feb. 7, 2008 Search Report dated Aug. 1, 2008.
PCT/US2008/053319 filed Feb. 7, 2008 Written Opinion dated Aug. 1, 2008.
PCT/US2008/053326 filed Feb. 7, 2008 Search Report dated Jul. 31, 2008.
PCT/US2008/053326 filed on Feb. 12, 2007 International Preliminary Report on Patentability dated Aug. 19, 2009.
PCT/US2008/053326 filed on Feb. 12, 2007 Written Opinion dated Jul. 31, 2008.
Siekmeyer, Steegmuller, Schrader, Hegel, Strobel, Schuessler, Novel Micro-Joining Techniques to Improve Stent Radiopacity, a Comparison of Welding and Riveting Processes, Proceedings of the MAterials & Processes for Medical Devices Conference, Boston (2005).
Standard Specification for Titanium and Titanium Alloy Bars and Billets.
Standard Specification for Unalloyed Titanium for Surgical Implant Applications UNS R50250, UNS R5044, UNS R50550, UNS R50700.
Stoeckel, Pelton, Duerig, Self-Expanding Nitinol Stents—Material and Design Considerations (ndc 2003).
U.S. Appl. No. 11/074,806, filed Mar. 8, 2005 Advisory Action dated Jul. 15, 2009.
U.S. Appl. No. 11/074,806, filed Mar. 8, 2005 Advisory Action dated Sep. 29, 2010.
U.S. Appl. No. 11/074,806, filed Mar. 8, 2005 Final Office Action dated Jul. 19, 2010.
U.S. Appl. No. 11/074,806, filed Mar. 8, 2005 Final Office Action dated May 13, 2009.
U.S. Appl. No. 11/074,806, filed Mar. 8, 2005 Non-Final Office Action dated Dec. 24, 2009.
U.S. Appl. No. 11/074,806, filed Mar. 8, 2005 Non-Final Office Action dated Jan. 18, 2013.
U.S. Appl. No. 11/074,806, filed Mar. 8, 2005 Non-Final Office Action dated Nov. 14, 2008.
U.S. Appl. No. 11/216,222, filed Aug. 31, 2005 Final Office Action dated Mar. 29, 2010.
U.S. Appl. No. 11/216,222, filed Aug. 31, 2005 Non-Final Office Action dated Aug. 18, 2009.
U.S. Appl. No. 11/216,228, filed Aug. 31, 2005 Final Office Action dated Aug. 12, 2009.
U.S. Appl. No. 11/216,228, filed Aug. 31, 2005 Final Office Action dated Jul. 26, 2007.
U.S. Appl. No. 11/216,228, filed Aug. 31, 2005 Non-Final Office Action dated Apr. 21, 2008.
U.S. Appl. No. 11/216,228, filed Aug. 31, 2005 Non-Final Office Action dated Mar. 6, 2007.
U.S. Appl. No. 11/216,228, filed Aug. 31, 2005 Non-Final Office Action dated Nov. 26, 2008.
U.S. Appl. No. 11/216,228, filed Aug. 31, 2005 Notice of Allowance dated Mar. 16, 2010.
U.S. Appl. No. 11/216,293, filed Aug. 31, 2005 Final Office Action dated Dec. 4, 2009.
U.S. Appl. No. 11/216,293, filed Aug. 31, 2005, Declaration of Achim Zipse Under 37 C.F.R. 1.132, Germany, dated Aug. 3, 2010.
U.S. Appl. No. 11/216,293, filed Aug. 31, 2005, Declaration of Thomas Haas Under 37 C.F.R. 1.132, Germany, dated Aug. 3, 2010.
U.S. Appl. No. 11/216,293, filed Aug. 31, 2009 Decision on Appeal dated Jul. 24, 2012.
U.S. Appl. No. 11/216,293, filed Aug. 31, 2009 Non-Final Office Action dated Feb. 1, 2013.
U.S. Appl. No. 11/216,293, filed Aug. 31, 2009 Non-Final Office Action Feb. 19, 2009.
U.S. Appl. No. 11/216,362, filed Aug. 31, 2005 Final Office Action dated Aug. 15, 2007.
U.S. Appl. No. 11/216,362, filed Aug. 31, 2005 Final Office Action dated Feb. 19, 2009.
U.S. Appl. No. 11/216,362, filed Aug. 31, 2005 Non-Final Office Action dated Dec. 13, 2007.
U.S. Appl. No. 11/216,362, filed Aug. 31, 2005 Non-Final Office Action dated Mar. 6, 2007.
U.S. Appl. No. 11/216,362, filed Aug. 31, 2005 Non-Final Office Action dated Sep. 30, 2009.
U.S. Appl. No. 11/216,362, filed Aug. 31, 2005 Non-Final Office Action dated Sep. 4, 2008.
U.S. Appl. No. 11/216,362, filed Aug. 31, 2005 Notice of Allowance dated Apr. 22, 2010.
U.S. Appl. No. 12/226,030, filed Mar. 31, 2009 Advisory Action dated Jan. 3, 2011.
U.S. Appl. No. 12/226,030, filed Mar. 31, 2009 Final Office Action dated Oct. 27, 2010.
U.S. Appl. No. 12/226,030, filed Mar. 31, 2009 Non-Final Office Action dated Apr. 12, 2010.
U.S. Appl. No. 12/226,030, filed Mar. 31, 2009 Non-Final Office Action dated Jul. 23, 2014.
U.S. Appl. No. 12/465,354, filed May 13, 2009 Non-Final Office Action dated Oct. 18, 2010.
U.S. Appl. No. 12/465,354, filed May 13, 2009 Notice of Allowance dated Jun. 17, 2011.
U.S. Appl. No. 12/526,711, filed Jun. 11, 2010 Final Office Action dated May 14, 2012.
U.S. Appl. No. 12/526,711, filed Jun. 11, 2010 Non-Final Office Action dated Dec. 7, 2011.
U.S. Appl. No. 13/687,874, filed Nov. 28, 2012 Non-Final Rejection dated May 30, 2014.
U.S. Appl. No. 13/687,977, filed Nov. 28, 2012 Non-Final Office Action dated Jun. 2, 2014.
U.S. Appl. No. 13/871,942, filed Apr. 26, 2013 Advisory Action dated Jul. 17, 2014.
U.S. Appl. No. 13/871,942, filed Apr. 26, 2013 Final Office Action dated Apr. 9, 2014.
U.S. Appl. No. 13/871,942, filed Apr. 26, 2013 Non-Final Office Action dated Nov. 26, 2013.
U.S. Appl. No. 15/282,661, filed Sep. 30, 2016 Non-Final Office Action dated Aug. 10, 2018.
U.S. Appl. No. 15/282,661, filed Sep. 30, 2016 Notice of Allowance dated Mar. 1, 2019.

(56) References Cited

OTHER PUBLICATIONS

U.S. Appl. No. 15/282,735, filed Sep. 30, 2016 Notice of Allowance dated Jan. 3, 2019.

* cited by examiner

HELICAL STENT HAVING IMPROVED FLEXIBILITY AND EXPANDABILITY

CROSS REFERENCE TO RELATED PATENT APPLICATION

This application is a continuation of U.S. patent application Ser. No. 13/970,474, now U.S. Pat. No. 9,554,927, filed Aug. 19, 2013, which is a continuation of U.S. patent application Ser. No. 11/074,806, now U.S. Pat. No. 8,512,391, filed Mar. 8, 2005, which is a continuation of U.S. patent application Ser. No. 10/231,666, now U.S. Pat. No. 6,878,162, filed Aug. 30, 2002; the disclosures of which are each incorporated by reference herein in their entirety.

BACKGROUND OF THE INVENTION

Field of the Invention

This invention relates broadly to arterial prosthesis. More particularly, this invention relates to vascular stents, and even more particularly to helical stents.

State of the Art

Transluminal prostheses are widely used in the medical arts for implantation in blood vessels, biliary ducts, or other similar organs of the living body. These prostheses are commonly known as stents and are used to maintain, open, or dilate tubular structures.

Stents are either balloon expandable or self-expanding. Balloon expandable stents are typically made from a solid tube of stainless steel. Thereafter, a series of cuts are made in the wall of the stent. The stent has a first smaller diameter configuration which permits the stent to be delivered through the human vasculature by being crimped onto a balloon catheter. The stent also has a second, expanded diameter configuration, upon the application, by the balloon catheter, from the interior of the tubular shaped member of a radially, outwardly directed force.

Self-expanding stents act like springs and recover to their expanded or implanted configuration after being compressed. As such, the stent is inserted into a blood vessel in a compressed state and then released at a site to deploy into an expanded state. One type of self-expanding stent is composed of a plurality of individually resilient and elastic thread elements defining a radially self-expanding helix. This type of stent is known in the art as a "braided stent". Placement of such stents in a body vessel can be achieved by a device which comprises an outer catheter for holding the stent at its distal end, and an inner piston which pushes the stent forward once it is in position. However, braided stents have many disadvantages. They typically do not have the necessary radial strength to effectively hold open a diseased vessel. In addition, the plurality of wires or fibers used to make such stents could become dangerous if separated from the body of the stent, where it could pierce through the vessel.

Therefore, recently, self-expanding stents cut from a tube of superelastic metal alloy have been manufactured. These stents are crush recoverable and have relatively high radial strength. U.S. Pat. No. 5,913,897 to Corso, U.S. Pat. No. 6,042,597 to Kveen, and WIPO Patent Application WO 01/89421-A2 (with inventors Cottone and Becker, and referred to herein as "Cottone") each teach superelastic cut-tubular stents having a helically wound configuration of repeating undulations. Bridge structures connect adjacent circumferential windings by extending between loop portions of undulations on adjacent windings. However, the bridge structures and arrangements do not maximize the torsional flexibility of the stents. In particular, Cottone describes a stent having a helical pattern of bridges (connections) connecting windings of the helix which is reverse in handedness from the undulations of the windings which form the central portion of the stent. The design described provides the stent with asymmetric characteristics that cause the stent to resist torsional deformations differently in one direction versus the other. In addition, each "helix of connections" forms a string of connections in which the connections are interrupted by only one and one-half undulations. As such, that string is resistant to stretching and compression. Accordingly, when a stent so designed is twisted torsionally, that string of connections causes constriction of the stent when twisted in the "tightening" direction (i.e., in the direction of the windings) and expansion of the stent when twisted in the opposite "loosening" direction. This differential torsional reaction results in the undulations of the stent being forced out of the cylindrical plane of the surface of the stent, such that the stent appears to buckle when twisted in the "loosening" direction.

In fact, even if the stent were constructed opposite to Cottone's preferred embodiment (that is, with a helix of bridges having the same handedness as the helix of undulations), the same effect results. Stents built with constructions containing a string of bridges separated by only a small number of undulations behave poorly when twisted. That is, they react differently if the stent is twisted one way versus the other, and the surface of the stent tends to buckle when twisted only slightly in the "loosening" direction.

Moreover, due to the helical windings of the stents, the stents described by Corso and Kveen terminate unevenly at the end of the helical windings. As such, the terminus of the final winding fails to provide a uniform radial expansion force 360° therearound. Cottone addresses this problem by providing a stent constructed with a helically wound portion of undulations in the central portion of the stent, a cylindrical portion of undulations at each end of the stent, and a transition zone of undulations joining each cylindrical portion to the central helically wound portion. The undulations of the transition zone include struts which progressively change in length.

Because the transition zone must mate directly to the cylindrical portion on one side and to a helically wound portion on the other side, the transition zone must create a free end from which the helical portion extends, must contain a bifurcation, and must depart from a uniform strut length for the struts around the circumference of the transition zone so that the transition from the helically wound portion to the cylindrical portion can occur.

However, if there are longer struts in a portion of the transition zone, that portion tends to expand more than the portion with shorter struts because the bending moments created by longer struts are greater than those created by shorter struts. Also, for the same opening angle between two such struts when the stent is in an expanded state, the opening distance between such struts is greater if the struts are longer. These two factors combine their effects in the portion of the transition zone with longer struts so that the apparent opening distances are much larger than in the portion where the struts are shorter. As such, the simple transition zone described by Cottone is not amenable to uniform expansion and compression, which is a requirement of an efficient self-expanding stent.

Moreover, except in the case of the Cottone helical stent which is provided with a transition zone, and except where there are different strut lengths in the undulations at the ends of a stent, stents generally contain struts of one length throughout their design. Accordingly, in order to achieve uniform opening of the stent, all the struts have substantially the same width as well as length.

SUMMARY OF THE INVENTION

It is therefore an object of the invention to provide a cut-tube self-expanding helical stent which has substantially equal torsional flexibility and resistance to torsional buckling when twisted in both directions.

It is another object of the invention to provide a cut-tube self-expanding helical stent having a transition zone and a cylindrical segment at each end thereof, and to improve the expandability of the transition zone.

It is a further object of the invention to provide a cut-tube self-expanding helical stent having a transition zone in which openings created between the struts of an expanded stent can be made more uniform over the entire transition zone.

In accord with the invention, which will be described in detail below, a cut-tube self-expanding stent having a central helically wound portion comprising repeating undulations formed of struts is provided at each of its ends with a cylindrical portion, and a transition zone between the helical portion and each cylindrical portion.

According to a first aspect of the invention, several criteria are set forth which together provide for optimal torsional flexibility and expandability in a self-expanding helically wound stent. According to a first criterion, the torsional flexibility of the stent is maximized by having all the "strings" of bridges which connect adjacent helical winding be interrupted by the maximum possible number of undulations. This results in these bridge strings being as stretchy and compressible as possible. According to a second criterion, the undulations in the central portion are interdigitated. According to a third criterion, preferred numbers of undulations, bridges, and undulations between bridges are provided. According to a fourth criterion, the bridges preferably extend in a "short" direction, longitudinally crosswise across the helically space separating the helical windings of undulations. Most preferably, the bridges join loops of undulations which are out of phase by one and one-half undulations.

According to a second aspect of the invention, uniform opening of the transition zone is achieved by altering the flexibility of a series of struts in accordance with their lengths. Specifically, the long transition zone struts are made wider (in the cylindrical plane) to compensate for the greater bending moments imposed by the longer struts. This keeps the opening distance (the distance between the open ends of adjacent struts in an expanded stent) approximately constant throughout the transition zone. More particularly, in a typical transition zone, the shortest strut must be approximately half the length of the longest strut. In order to maintain similar opening distances, the long struts should be wider by approximately the cube root of 2 squared, i.e. approximately 1.59. The ratio may be adjusted to a value near this ratio in order to achieve a uniform opening, giving consideration to the fact that in a transition zone two adjacent struts of unequal length both contribute to the bending moment on the flexing connection that joins them. The ratio may also be adjusted to make the opening angle of the shortest strut pairs not exceed a certain value in order to limit the maximum strains experienced in that portion of the transition zone.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
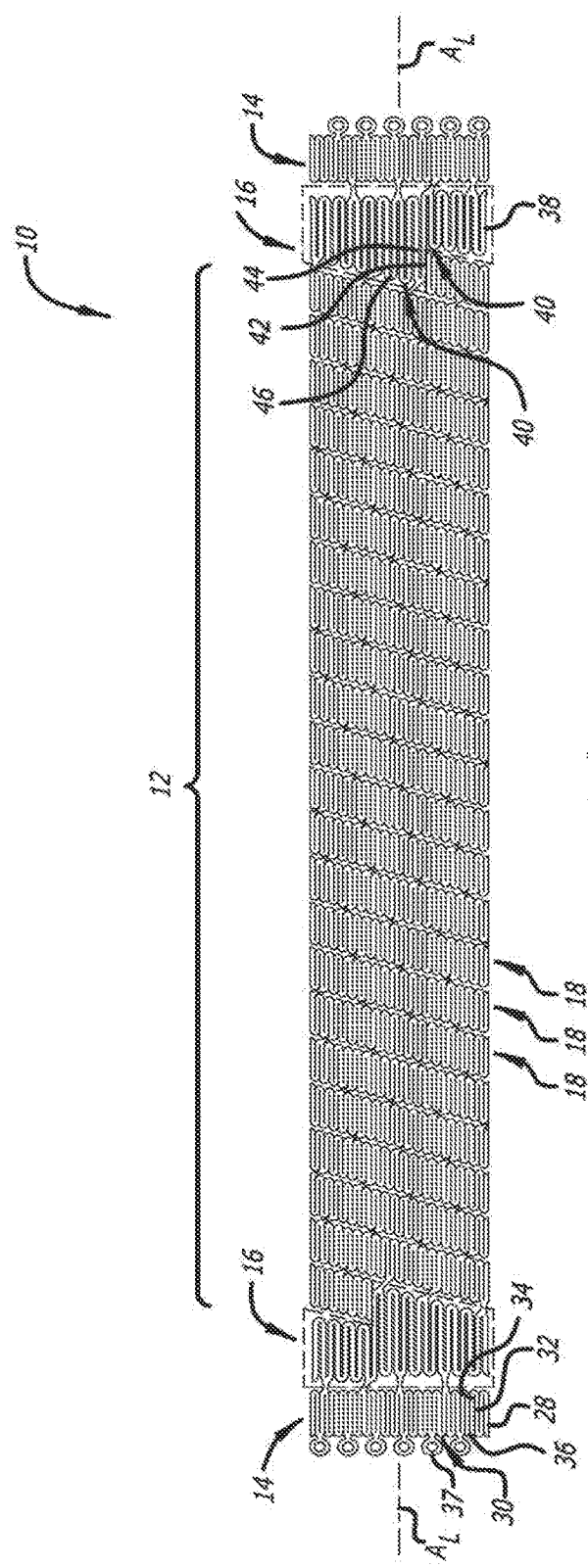
FIG. 1 is a broken flattened view of a helical stent according to the invention in an unexpanded state, wherein the stent has been cut parallel to its longitudinal axis and laid flat.

Turning now to FIG. 1, a helical stent 10 according to the invention is shown. The stent has a collapsed configuration with a first smaller diameter for insertion into a body vessel, and self-expands to an expanded or deployed configuration with a second larger diameter for deployment within the vessel. The stent is preferably a laser-cut tubular construction of a superelastic metal alloy such as nickel-titanium.

Figure 2:
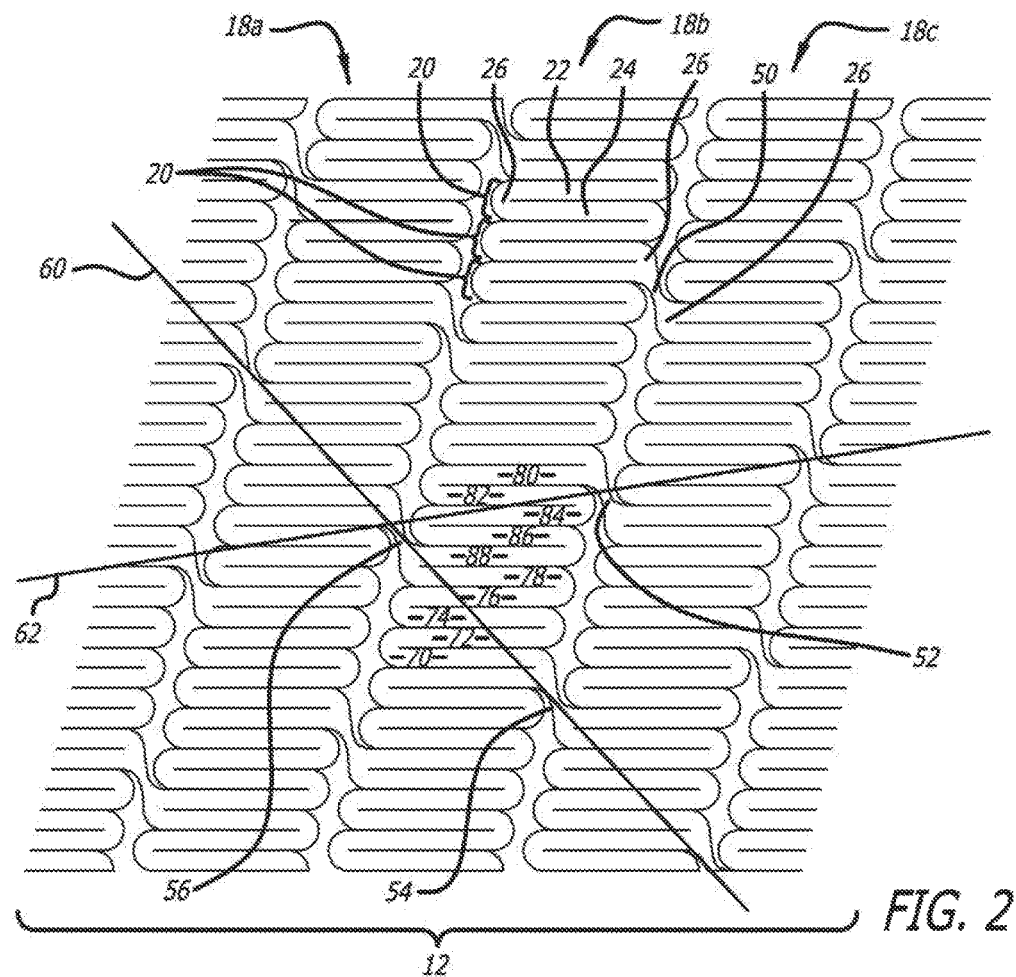
FIG. 2 is an enlarged broken flattened view of a central portion of the helical stent of FIG. 1.

The stent 10 includes a central portion 12, a cylindrical portion 14 at each end of the stent 10, and a transition zone 16 between the central portion 12 and each cylindrical end portion 14. The central portion 12 is comprised of a plurality of helical circumferential windings (single turns of a helix) 18 of substantially like undulations (in length and width) 20, with each undulation 20 being defined by two adjacent struts, e.g., struts 22, 24, and a loop 26 connecting the struts (FIG. 2). The cylindrical end portion 14 is comprised of preferably a single cylindrical winding 28 of like undulations 30, with each such undulation 30 being defined by two adjacent struts, e.g., struts 32, 34, and a loop 36 connecting the struts. Optionally, one or more structures 37 adapted to receive or otherwise be coupled to radiopaque markers (not shown) can be provided at the ends of one or more of the undulations 30. The transition zone 16 is comprised of preferably a single winding 38 of undulations 40 that preferably progressively increase in size, with each such undulation 40 being defined by two adjacent struts, e.g., struts 42, 44, and a loop 46 connecting the struts.

In each of sections 12, 14 and 16 the undulations 20, 30, 40 extend in a generally longitudinal direction. That is, when the stent is in a collapsed configuration, as shown in FIG. 1, struts of the helical portion (e.g., 22 and 24), cylindrical portion (e.g., 32 and 34) and transition zone (e.g., 42 and 44) all extend substantially parallel to the longitudinal axis AL of the stent. In the expanded configuration, adjacent struts are moved apart and angled relative to each other.

Referring to FIG. 2, particularly with respect to the central portion 12, as the windings 18a, 18b, 18c are longitudinally displaced along the length of the stent, bridges, e.g. 50, 52, 54 and 56, are provided to connect together the loops 26 of undulations 20 on adjacent windings, e.g. 18a and 18b, and 18b and 18c, to prevent stent unwinding. The bridges 50, 52, 54, 56 can be seen to be arranged in right-handed and left-handed helical "strings" (right-handed string 60 and left-handed string 62) which extend about the stent.

There are several preferred design considerations (criteria) which, according to the invention, are preferably used together to identify a desired number and placement of undulations in any winding and a number and placement of bridges 50, 52, 54, 56 which connect together loops 26 of undulations on adjacent windings (and thereby connect together the windings 18a, 18b, 18c). If the central portion 12 is designed in accord with the following criteria, the central portion 12 will have a desired torsional flexibility and expandability; i.e., be not too stiff, but also be sufficiently flexible so that the central portion 12 will not be subject to kinking.

In accord with a first criterion, the pattern of bridges is as symmetric as possible. That is, the right-handed and left-handed strings 60, 62 of bridges should be as similar as possible. Further, the torsional flexibility of the stent is maximized by having each string 60, 62 of bridges be interrupted by the maximum possible number of undulations 20. This results in the bridge strings being as stretchy and compressible as possible. In any given stent design, there is a certain number of undulations which form a complete circumferential winding (single turns of the helical portion). The number of undulations 20 which separate the bridges lying along any one string depends, therefore, on the number of bridges within a complete circumferential winding. For example, if there are eighteen undulations around a circumferential winding and three bridges, and if the bridges on adjacent windings are staggered, in accord with the invention there should be three undulations separating bridges along each helical strings of bridges.

In accord with a second criterion, it is preferred that the loops 26 of the undulations 20 of the central portion 12 be interdigitated between the loops of the undulations on an adjacent winding. For example, if there are eighteen undulations around the circumference, each undulation would be rotationally displaced from the undulations on the adjacent winding by one-half an undulation (i.e., one thirty-sixth of a circle or ten degrees), so that the "peak" of one loop is directed into the "valley" between two loops on an adjacent winding.

In accord with a third criterion, it is necessary to observe how the number (m) of undulations between bridges and the number (n or n+½) of undulations around the circumference interact to create helical strings of bridges. That is, with an increase in n for a stent of a given diameter, the stent is weakened and subject to kinking. This is because, for a stent of a given diameter, by providing more struts, narrower and weaker struts must be used. As n is decreased, the struts are increased in width and thus stiffness. However, while this may strengthen the stent, the stent is nevertheless limited in flexibility and may be undesirably stiff. In accord with the invention, for the optimum combination of strength and flexibility, it is preferred that n (i.e. the number of undulations) be sixteen to twenty, and more preferably eighteen to nineteen, where n may optionally be a non-integer. In addition, the number of bridges, m, for the preferred number of struts is most preferably three to five bridges per circumferential winding.

In accord with a fourth criterion, consideration must be made as to the locations between which the bridges connect and the direction in which the bridges extend. In accord with the preferred interdigitated criterion, the bridges cannot extend parallel to the longitudinal axis AL of the stent. Rather, they preferably extend across loops located one and one-half pitches away; i.e., each bridge connects over two struts relative to directly across from the strut from which the bridge extends. In addition, the bridges extend longitudinally crosswise across the helical space separating the adjacent loops (i.e. in a "short" direction), as opposed circumferentially along the helical space separating the adjacent loops (i.e., in a "long" direction).

In view of the above, a preferred exemplar central portion 12 of the stent 10 illustrating the application of the above criteria is now described. Referring to FIG. 2, the central portion 12 of the stent 10 includes repeating undulations 20 (each comprising two struts 22, 24 and a loop 26) that are helically wound in circumferential windings 18a, 18b, 18c, etc. There are preferably nineteen undulations 20 in each circumferential winding 18a, 18b, 18c and the undulations are interdigitated. With reference to windings 18b and 18c, a bridge 50, 52, 54 is located every five undulations therebetween, and each bridge joins loops of undulations on the adjacent windings 18a, 18b which are one and one-half pitches away (or two struts over from directly across) in the "short" direction. That is, all bridges in the central portion 12 of the stent preferably extend in the same direction, longitudinally crosswise across the helical space. This preferred exemplar embodiment provides a very symmetrical distribution of bridges. In particular, traveling from any one bridge, e.g. bridge 54, to the next bridge, e.g. bridge 56, along the right-hand string 60 of bridges, traverses exactly two and one half undulations (or five struts 70, 72, 74, 76 and 78). Moreover, traveling from any one bridge, e.g. bridge 52, to the next bridge, e.g. bridge 56, along the left-handed string 62 of bridges, also traverses exactly two and one half undulations (or five struts 80, 82, 84, 86 and 88). This design gives very even torsional flexibility and expandability, and the stent may be twisted considerably in either direction without buckling.

Figure 3:
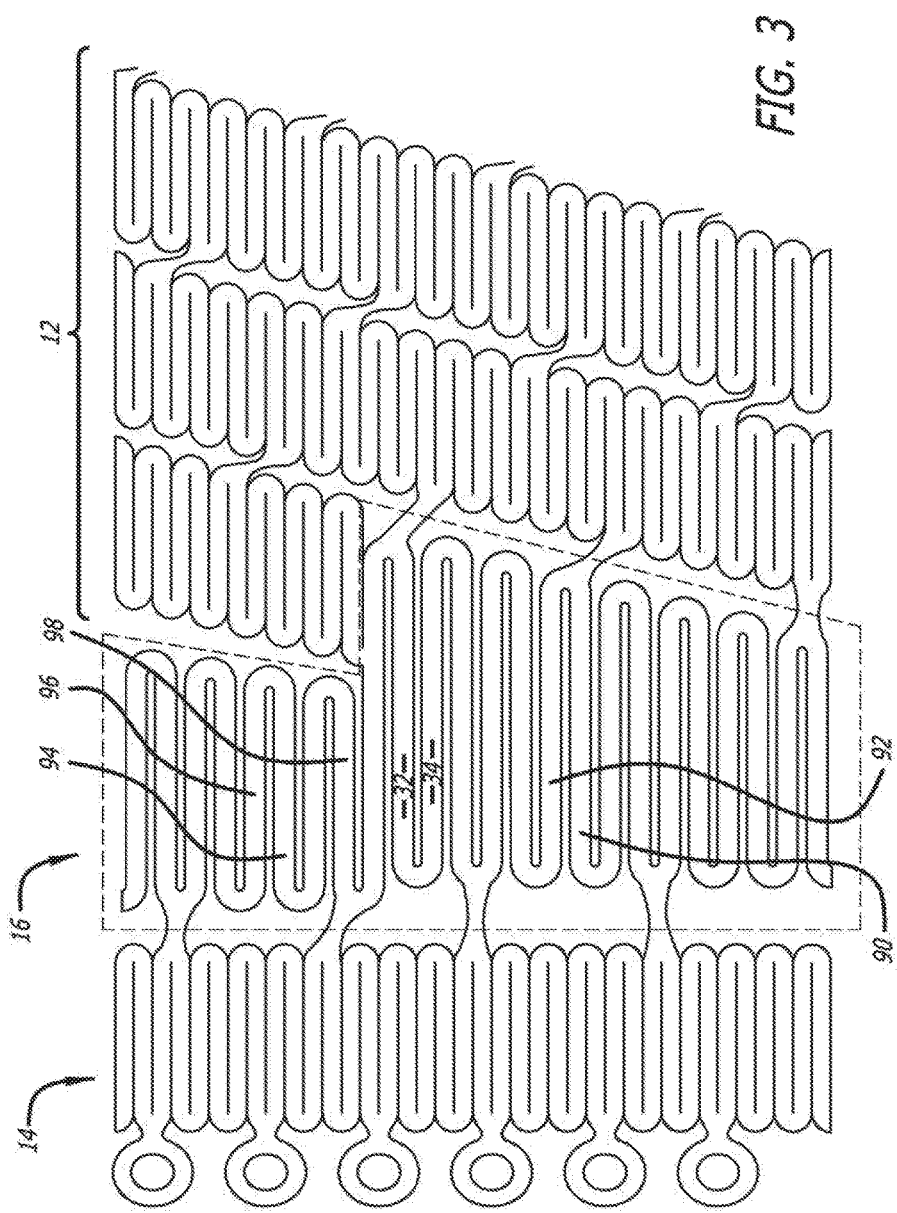
FIG. 3 is an enlarged broken flattened view of a transition zone portion of the helical stent of FIG. 1.

Referring now to FIG. 3, the transition zone 16 of the stent 10 is shown. The transition zone, as stated above, includes struts that progressively increase in length. The long transition zone struts 90, 92 are relatively wider (in the cylindrical plane) than the shorter transition zone struts 94, 96 to compensate for the greater bending moments imposed by the longer struts. Moreover, even the shortest transition zone strut 98 is preferably longer and wider than the struts 22, 24 of the central portion 12. In the embodiment shown in FIG. 3, a terminal end of a strut of the central portion 12 adjoins one longer strut between the opposing ends of the one longer strut. In this embodiment, the one longer strut is connected to the shortest transition zone strut 98.

Figure 4:
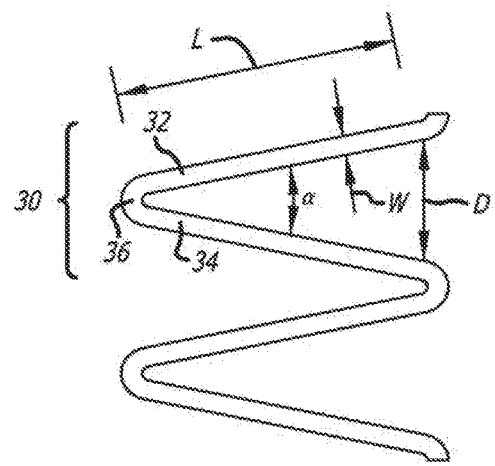
FIG. 4 is a schematic view of a plurality of struts of the transition zone of FIG. 3 shown in an open configuration.

More particularly, referring to FIGS. 3 and 4, for substantially uniform expansion of the stent, it is desirable for the opening distance D (i.e., the distance between the ends of two adjacent struts, e.g. struts 32 and 34, when the stent is in an open configuration) to be approximately even throughout the transition zone 16. Accordingly, the opening angle a between pairs of longer struts in the transition zone, e.g. struts 32 and 34, must be smaller than the opening angle a between shorter struts, e.g. struts 94 and 96. In addition, the bending stiffness of the longer struts must be even greater than in proportion to their increased bending moment. The bending stiffness S of a rectangular-section beam is in proportion to the third power of the width (in the bending direction) W. As such, by way of example, in order to double the bending stiffness of a strut, the width W of the strut must be increased by the cube root of two.

The bending moment M of a strut is in linear proportion to the length L of the strut. The opening angle a is proportional to the bending moment M divided by the stiffness S. The opening distance D is proportional to the product of the opening angle a multiplied by strut length L. Therefore, the opening distance D is proportional to a*L, which is equal to (M/S)*L. Since M is linearly proportional to L, the opening distance D is proportional to the square of L divided by stiffness S. In order to keep the opening distance D between adjacent struts (i.e., pairs of struts) equal throughout the transition zone 16, the stiffness of the bending segments of the struts must be in proportion to the square of their lengths. Hence, the cube of the width must be proportional to the square of the length:

$W^3$ is proportional to $L^2$

In a preferred transition zone, the shortest strut 98 should be approximately half the length of the longest strut 42. Therefore, in order to maintain similar opening distances, the longer struts are most preferably wider by the cube root of 2 squared, or 1.59, relative to the shorter struts. The ratio may be adjusted to a value near this ratio (e.g., ±25%, or 1.19 to 1.99) in order to achieve a uniform opening, giving consideration to the fact that in a transition zone two adjacent struts of unequal length both contribute to the bending moment on the flexing connection that joins them. It may also be desirable to make the opening angle a between the shortest strut pairs not exceed a certain value in order to limit the maximum strains experienced in that portion of the transition zone.

As such, uniform opening is achieved in the transition zone by altering the flexibility of a series of struts in accordance with their lengths.

There have been described and illustrated two aspects of a preferred stent relating to the helical central portion and the transition zone. While particular embodiments of the invention have been described, it is not intended that the invention be limited thereto, as it is intended that the invention be as broad in scope as the art will allow and that the specification be read likewise. Thus, the two preferred aspects (relating to the central helical portion and the transition zone) can be used together or separately. Moreover, each of the design considerations relating to the helical central portion can be used alone or together with one or more of the other considerations. It will therefore be appreciated by those skilled in the art that yet other modifications could be made to the provided invention without deviating from its spirit and scope as claimed.

What is claimed is:

1. A stent comprising:
    a tubular member including:
        a central portion comprising a plurality of helical windings separated by a helical space, each of the plurality of helical windings including a plurality of undulations, each of the plurality of undulations comprising two adjacent struts and a loop connecting the struts, wherein:
            a plurality of bridges connects loops of a first winding of the plurality of helical windings to loops of a second adjacent winding of the plurality of helical windings, and
            a same number of struts is traversed on the first winding and the second adjacent winding between adjacent bridges of the plurality of bridges; and
        cylindrical end portions; and
        a transition zone between the central portion and each of the cylindrical end portions, the transition zone including a plurality of transition undulations having transition zone struts that increase in length.

2. The stent of claim 1, wherein the loops of the plurality of undulations on adjacent windings of the plurality of helical windings are interdigitated.

3. The stent of claim 2, wherein the bridges extend between loops located one and one-half pitches away.

4. The stent of claim 3, wherein the first winding of the plurality of helical windings includes sixteen to twenty undulations.

5. The stent of claim 4, wherein the first winding of the plurality of helical windings includes eighteen to nineteen undulations.

6. The stent of claim 5, wherein the first winding of the plurality of helical windings includes three to five bridges.

7. The stent of claim 1, wherein each of the plurality of bridges in the central portion extends in a same direction in a cylindrical plane of the stent.

8. The stent of claim 7, wherein each of the plurality of bridges extends longitudinally across the helical space.

9. The stent of claim 8, wherein the stent is self-expanding.

10. The stent of claim 1, wherein a longer strut of the transition undulations has a wider width than a shorter strut of the transition undulations.

11. A stent comprising:
    a tubular member including a central portion having two ends, the central portion comprising a plurality of helical windings separated by a helical space, each of the plurality of helical windings including a plurality of undulations, each of the plurality of undulations comprising two adjacent struts and a loop connecting the struts,
    cylindrical end portions at each of the two ends of the central portion, and
    transition zones between the central portion and each of the cylindrical end portions, the transition zones including a plurality of transition undulations having struts that increase in length, wherein a longer strut of the transition undulations has a wider width than a shorter strut of the transition undulations.

12. The stent of claim 11, wherein a longest strut of the transition undulations is 1.19 to 1.99 times wider than a shortest strut of the transition undulations.

13. The stent of claim 11, wherein a longest strut of the transition undulations is approximately 1.59 times wider than a shortest strut of the transition undulations.

14. The stent of claim 11, wherein the struts of the central portion are all of a common length and width.

15. The stent of claim 14, wherein the common length of the struts of the central portion is shorter than a shortest length of the struts of the transition undulations, and wherein the common width of the struts of the central portion is narrower than a narrowest width of the struts of the transition undulations.

* * * * *